(12) United States Patent
Hong

(10) Patent No.: US 7,825,130 B2
(45) Date of Patent: Nov. 2, 2010

(54) PTEN INHIBITOR OR MAXI-K CHANNELS OPENER

(75) Inventor: Ki Whan Hong, Busan (KR)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 972 days.

(21) Appl. No.: 10/546,632

(22) PCT Filed: Feb. 24, 2004

(86) PCT No.: PCT/JP2004/002146

§ 371 (c)(1),
(2), (4) Date: Aug. 24, 2005

(87) PCT Pub. No.: WO2004/075897

PCT Pub. Date: Sep. 10, 2004

(65) Prior Publication Data

US 2006/0154963 A1    Jul. 13, 2006

Related U.S. Application Data

(60) Provisional application No. 60/449,435, filed on Feb. 25, 2003, provisional application No. 60/449,589, filed on Feb. 26, 2003.

(51) Int. Cl.
A61K 38/41 (2006.01)

(52) U.S. Cl. .................................................. 514/312

(58) Field of Classification Search ................. 546/159, 546/163; 514/312
See application file for complete search history.

(56) References Cited

U.S. PATENT DOCUMENTS

| | | | |
|---|---|---|---|
| 4,277,479 A | | 7/1981 | Nishi et al. |
| 6,019,735 A * | | 2/2000 | Kensey et al. ............... 600/573 |
| 6,187,790 B1 | | 2/2001 | Cutler |
| 6,267,985 B1 * | | 7/2001 | Chen et al. .................. 424/451 |
| 6,294,192 B1 * | | 9/2001 | Patel et al. .................. 424/451 |
| 6,322,524 B1 * | | 11/2001 | Kensey et al. ............... 600/573 |
| 6,322,525 B1 * | | 11/2001 | Kensey et al. ............... 600/573 |
| 6,451,339 B2 * | | 9/2002 | Patel et al. .................. 424/451 |
| 6,458,804 B1 * | | 10/2002 | Cutler et al. ................. 514/312 |
| 6,571,608 B2 * | | 6/2003 | Shin et al. ................... 73/54.01 |
| 6,624,435 B2 * | | 9/2003 | Kensey et al. ............... 250/577 |
| 6,743,806 B2 | | 6/2004 | Hong |

FOREIGN PATENT DOCUMENTS

| JP | 4-159224 | 6/1992 |
|---|---|---|
| JP | 7-76584 | 3/1995 |
| JP | 9-157170 | 6/1997 |

OTHER PUBLICATIONS

Kim, J of Pharm and Exp Therap, 2004, vol. 308(1), pp. 97-104.*
Hong, J of Pharm and Exp Therap, 2003, vol. 306(3), pp. 1182-1190.*
Abstract of J Pharmacol Exp Ther. Sep. 2003; 306(3): 1182-90. Epub Jun. 13, 2003.
Abstract of J Pharmacol Exp Ther. Jan. 2004; 308(1): 97-104. Epub Oct. 20, 2003.
Abstract of Journal of Pharmacology And Experimental Therapeutics Fast Forward First published on Jun. 13, 2003; DOI: 10.1124/jpet.103.052365.
CNS Drug Reviews vol. 3. No. 4 pp. 427-437 (XIVth World Congress of Pharmacology, San Francisco, CA USA Jul. 7-12, 2002 New Drugs for the Treatment of Central Nervous System Disorders).

* cited by examiner

Primary Examiner—D. Margaret Seaman
(74) Attorney, Agent, or Firm—Finnegan, Henderson, Farabow, Garrett & Dunner, LLP

(57) ABSTRACT

A new PTEN opener or a new opener of a large conductance $Ca^{2+}$-activated $K^+$ channel (Maxi-K channel) which comprises as an active ingredient a tetrazolylalkoxy-dihydrocarbostyril compound of the formula (I):

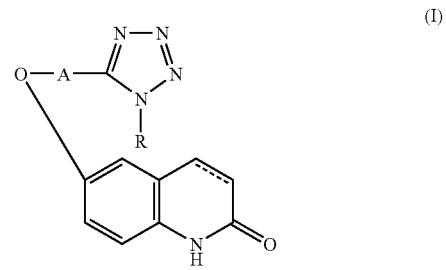

wherein R is cycloalkyl, A is lower alkylene, and the bond between 3- and 4-positions of the carbostyril nucleus is single bond or double bond, or a salt thereof, which is useful as a medicament for promotion of the survival of normal cells, brain cells, heart cells, and skin, and further for inhibiting of Gram negative sepsis and cell migration and cell invasion due to inhibition of PTEN and is further useful as a medicament for the treatment of neuronal disorders, for example, an anticonvulsant, a neuroprotecting agent, a medicament for treatment of regional cerebral edema and neurologic motor impairment, cognitive disorders, traumatic brain injury, Parkinson's disease, epilepsy, migraine, and Alzheimer's disease, etc.

2 Claims, 4 Drawing Sheets

$P < 0.01$ vs. absence of TNF-α and cilostazol.
*$P < 0.05$; **$P < 0.01$ vs. TNF-α alone.
† $P < 0.05$ vs. cilostazol (10 µM) alone.

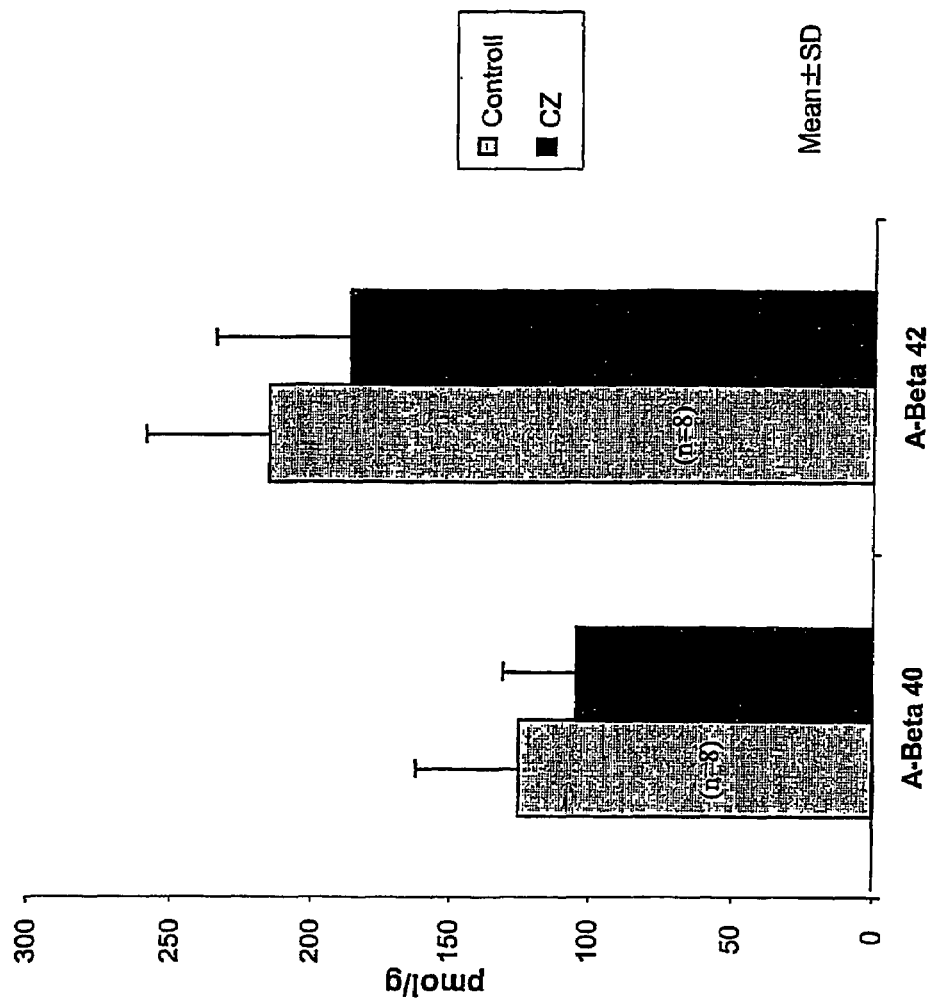

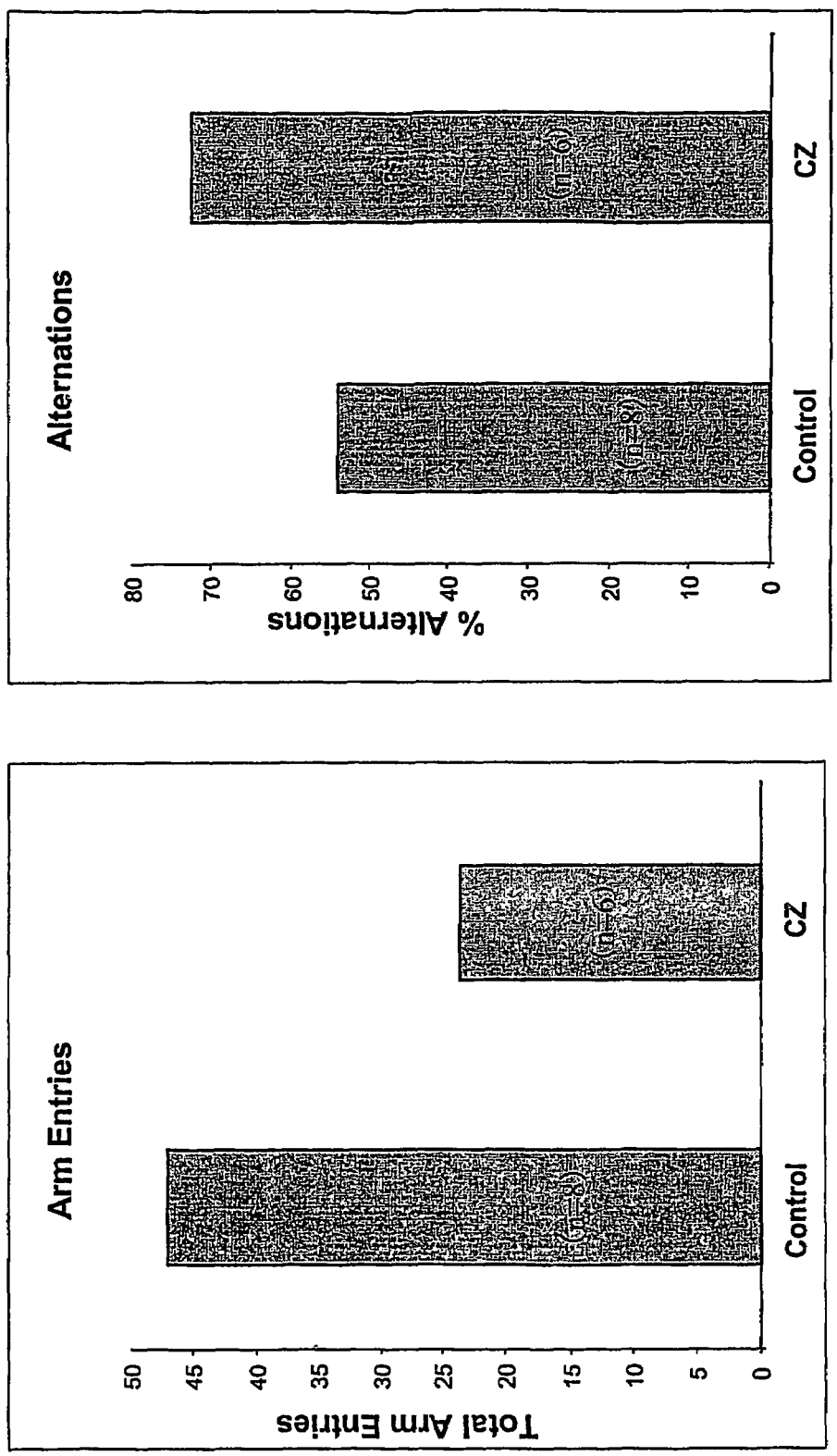

PTEN INHIBITOR OR MAXI-K CHANNELS OPENER

This application is a national phase application of international application number PCT/JP2004/002146, filed Feb. 24, 2004 and claims the benefit of provisional application Nos. 60/449,435, filed Feb. 25, 2003, and 60/449,589, filed Feb. 26, 2003, respectively, the content of all of which are incorporated herein by reference.

TECHNICAL FIELD

The present invention relates to a new PTEN inhibitor or a new Maxi-K channels opener. More particularly, it relates to a PTEN inhibitor or new Maxi-K channels opener, which comprises as an active ingredient a tetrazolylalkoxy-dihydrocarbostyril compound of the formula (I):

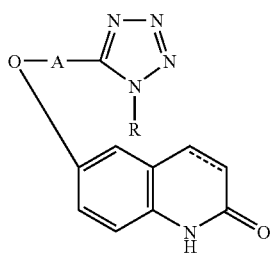

wherein R is a cycloalkyl group, A is a lower alkylene group, and the bond between 3- and 4-positions of the carbostyril nucleus means a single bond or a double bond, or a salt thereof.

TECHNICAL BACKGROUND

PTEN (Phosphatase and Tensin homolog deleted on chromosome Ten) was isolated as a tumor suppressor gene in 1997, and since then the physiological functions thereof have been analyzed from various viewpoints. It is reported in 1998 that the PTEN gene product exhibits a new phosphatase activity, i.e. it is able to dephosphorylate a phosphatidylinositol 3,4,5-trisphosphate (PIP3) substrate, which is a lipid second messenger, at D3 position thereof (cf. Beitner-Johnson D, Millhorn DE., J. Biol. Chem., 273: pp. 13375-13378, 1998).

In view of the functions of PTEN, it is expected that when inhibition of PTEN will be effective for promotion of the survival of normal cells, brain cells, heart cells, and skin, and further effective for inhibiting of Gram negative sepsis and cell migration and cell invasion.

Besides, it is known that the opening of potassium channel induces flowing the intracellular potassium ion out of cells which results in negative intracellular potential and that the potassium channel is voltage-dependent and is controlled intracellular calcium concentration and intracellular ATP. Maxi-K channel is a class of large conductance calcium sensitive potassium channels, and the activity of Maxi-K channels is controlled by intracellular calcium concentration and membrane potential, etc. The Maxi-K channels are widely distributed within the living body such as neurons, heart cells, smooth muscle cells, and the opening of the Maxi-K channels induces hyperpolarization of cells. It is also known that the opening of the Maxi-K channels is useful for the treatment of neuronal disorders, for example, as a medicament such as (1) an anticonvulsant, (2) a medicine for neuroprotection, for treatment of regional cerebral edema and neurologic motor impairment, cognitive disorders, traumatic brain injury, Parkinson's disease, epilepsy, migraine, and Alzheimer's disease, (3) a medicine for control of a pain, (4) a medicine for treating urge urinary incontinence, intestinal hypermotility, uterine contractility, anxiety, and depression.

DISCLOSURE OF THE INVENTION

During the studies on PTEN, the present inventor has found that the tetrazolylalkoxy-dihydrocarbostyril compounds of the formula (I) or a salt thereof as mentioned above, particularly 6-[4-(1-cyclohexyl-1H-tetrazol-5-yl)butoxy]-3,4-dihydro-carbostyril or a salt thereof, which are known to have platelet aggregation inhibitory activity and vasodilating activity, exhibit an activity of inhibiting PTEN and hence are useful as a PTEN inhibitor, and then the present invention has been accomplished.

Further, during the studies on functional analysis of Maxi-K channels, the present inventor has found that the tetrazolylalkoxy-dihydrocarbostyril compounds of the formula (I) or a salt thereof as mentioned above, particularly 6-[4-(1-cyclohexyl-1H-tetrazol-5-yl)butoxy]-3,4-dihydro-carbostyril or a salt thereof, which are known to have platelet aggregation inhibitory activity and vasodilating activity, exhibit an activity of opening of Maxi-K channels and hence are useful as a Maxi-K channels opener, and then the present invention has been accomplished.

BRIEF DESCRIPTION OF THE DRAWINGS

FIG. 2A shows the effects of cilostazol (tradename of 6-[4-(1-cyclohexyl-1H-tetrazol-5-yl)butoxy]-3,4-dihydrocarbostyril), FIG. 2B shows effects of cilostazol and/or glibenclamide (abbreviated as "GBC", which is commercially available antidiabetics, suggestive of absence of opening of ATP-sensitive K$^+$ channels), and FIG. 2C shows effects of cilostazol and/or iberiotoxin (abbreviated as "Ibtx", which is known as Maxi-K$^+$ channel blocker, suggestive of opening of Maxi-K$^+$ channels).

FIG. 3 shows total amyloid-beta concentration (A-Beta 40 and A-Beta 42 levels) in brains of mice in the control and cilostazole treated groups which were detected by ELISA.

FIG. 4 shows a summary of experimental results obtained from the Y-maze behavior paradigm for testing the effects on Alzheimer's disease of the compound of the present invention.

DETAILED DESCRIPTION OF THE INVENTION

Figure 1:
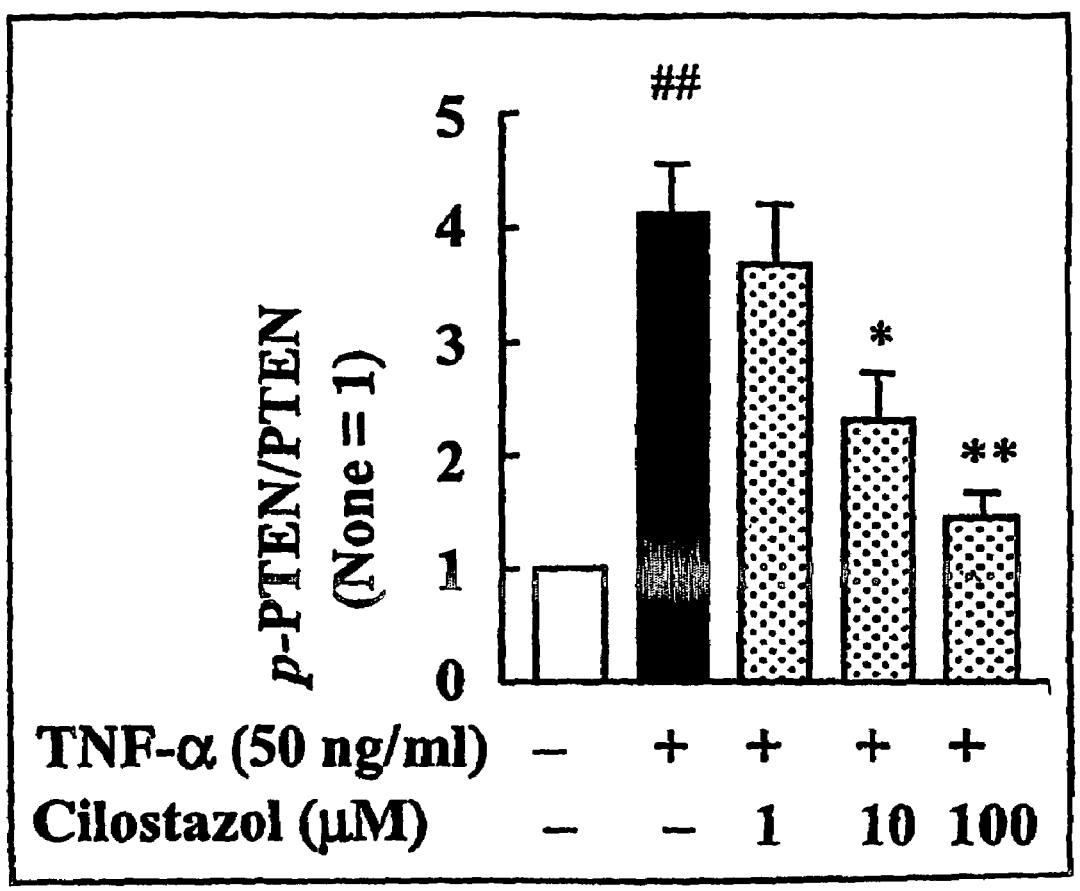
FIG. 1 shows a suppression of the TNF-α (50 ng/ml)-stimulated increased PTEN phosphorylation level by cilostazol (tradename of 6-[4-(1-cyclohexyl-1H-tetrazol-5-yl)butoxy]-3,4-dihydro-carbostyril).

The present invention provides a new PTEN inhibitor or new Maxi-K channels opener which comprises as an active ingredient a tetrazolylalkoxy-carbostyril compound of the formula (I) or a salt thereof. The present invention further provides a method for inhibiting PTEN and a method for opening Maxi-K channels, which comprises administering the tetrazolylalkoxy-carbostyril compound (I) or a salt thereof to a patient in need of such treatments, and further provides a use of the tetrazolylalkoxy-carbostyril compound (I) or a salt thereof for inhibiting PTEN as well as for opening Maxi-K channels.

The compound of the formula (I) or a salt thereof has excellent PTEN inhibitory effect and hence the PTEN inhibitor of the present invention comprising as an active ingredient the compound of the formula (I) or a salt thereof is useful as a medicament for promotion of the survival of normal cells, brain cells, heart cells, and skin, and further for inhibiting of Gram negative sepsis and cell migration and cell invasion without any side effect due to inhibition of PTEN.

Furthermore, the compound of the formula (I) or a salt thereof has excellent effect of opening of a large conductance calcium-activated K$^+$ channel (Maxi-K channels) and hence the Maxi-K channel opener of the present invention comprising as an active ingredient the compound of the formula (I) or a salt thereof is useful as a medicament for the treatment of neuronal disorders, for example, an anticonvulsant, a neuroprotecting agent, a medicament for treatment of regional cerebral edema and neurologic motor impairment, cognitive disorders, traumatic brain injury, Parkinson's disease, epilepsy, migraine, and Alzheimer's disease, pain, urge urinary incontinence, intestinal hypermotility, uterine contractility, anxiety, and depression.

The tetrazolylalkoxy-dihydrocarbostyril compounds of the formula (I) and processes for preparation thereof are disclosed in JP-63-20235.

In the formula (I), the "cycloalkyl group" includes $C_{3-8}$ cycloalkyl groups such as cyclopropyl, cyclobutyl, cyclopentyl, cyclohexyl, cycloheptyl, cyclooctyl, etc. but preferable one is cyclohexyl. The "lower alkylene group" includes $C_{1-6}$ alkylene groups such as methylene, ethylene, propylene, butylene, etc. but preferable one is butylene.

Particularly preferred compound is 6-[4-(1-cyclohexyl-1H-tetrazol-5-yl)butoxy]-3,4-dihydro-carbostyril, which has been sold as a vasodilator under a tradename of cilostazol.

The compound of the formula (I) of the present invention can be used in bulk or preferably in the form of a pharmaceutical preparation with a conventional pharmaceutical carrier or diluent. The dosage form is not limited to a specific form, but may be in any conventional dosage forms, for example, preparations for oral administration, such as tablets, capsules, granules, various liquid preparations suitable for oral administration, or preparations for parenteral administration, such as injections, suppositories. The dosage is not limited to a specific range but is usually in the range of 100 to 400 mg per day in adult (50 kg of body weight) which is administered once or being divided in one to several times. The active compound is preferably contained in the preparation in an amount of 50 to 100 mg per dosage unit.

The preparation for injection is usually prepared in the form of a liquid preparation, an emulsion, or a suspension, which are sterilized and further are preferably made isotonic to the blood. The preparations in the form of a liquid, emulsion or suspension are usually prepared by using conventional pharmaceutical diluents, for example, water, ethyl alcohol, propylene glycol, ethoxylated isostearyl alcohol, polyoxylated isostearyl alcohol, polyoxyethylene sorbitan fatty acid esters. These preparations may be incorporated with an isotonic agent such as sodium chloride, glucose, glycerin in an amount sufficient for making isotonic and may further incorporated with conventional solubilizers, buffers, anesthetizing agents, and optionally colorants, preservatives, fragrant materials, flavors, sweetening agents, and other medicaments.

The preparations such as tablets, capsules, liquid for oral administration may be prepared by a conventional method. The tablets may be prepared by mixing with conventional pharmaceutical carriers such as gelatin, starches, lactose, magnesium stearate, talc, gum arabic, and the like. The capsules may be prepared by mixing with inert pharmaceutical fillers or diluents and filled in a hard gelatin capsule or a soft capsule. The oral liquid preparations such as syrups or elixirs are prepared by mixing the active compound and sweetening agents (e.g. sucrose), preservatives (e.g. methylparaben, propylparaben), colorants, flavors, and the like. The preparations for parenteral administration may also be prepared by a conventional method, for example, by dissolving the compound (I) of the present invention in a sterilized aqueous carrier, preferably water or a saline solution. Preferred liquid preparation suitable for parenteral administration is prepared by dissolving about 50-100 mg of the active compound (I) in water and an organic solvent and further in a polyethylene glycol having a molecular weight of 300 to 5000, which is preferably incorporated with a lubricant such as sodium carboxy-methylcellulose, methyl-cellulose, polyvinylpyrrblidone, and polyvinyl alcohol. The above liquid preparations may preferably be further incorporated with a disinfectant (e.g. benzyl alcohol, phenol, thimerosal), a fungicide, and further optionally with an isotonic agent (e.g. sucrose, sodium chloride), a topical anesthetic, a stabilizer, a buffer, and the like. In view of keeping stability, the preparation for parenteral administration may be filled in a capsule, followed by removing the aqueous medium by a conventional lyophilizing technique, and is recovered into a liquid preparation by dissolving in an aqueous medium when used.

BEST MODE FOR CARRYING OUT THE INVENTION

The present invention is illustrated by the following preparation examples and experiments of suppressing effects of the compounds on the increase of PTEN phosphorylation which is stimulated by TNF-α or on the Maxi-K$^+$ channel opening, but should not be construed to be limited thereto.

Preparation 1

Preparation of Injection Preparation:

| Components | Amount |
| --- | --- |
| 6-[4-(1-Cyclohexyl-1,2,3,4-tetrazol-5-yl)butoxy]-3,4-dihydrocarbostyril | 5 g |
| Polyethyleneglycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The above parabens, sodium metabisulfite and sodium chloride are dissolved in a half amount of the above distilled water with stirring at 80° C. The mixture is cooled to 40° C., and thereto are dissolved the active compound, and further polyethylene glycol and polyoxyethylene sorbitan monooleate. The remaining distilled water for injection is added to the mixture, sterilized by filtering with a filter paper to give the desired injection preparation.

Preparation 2

Preparation of Tablets:

| Components | Amount |
|---|---|
| 6-[4-(1-Cyclohexyl-1,2,3,4-tetrazol-5-yl)butoxy]-3,4-dihydrocarbostyril | 100 g |
| Lactose (Japanese Pharmacopeia) | 40 g |
| Cornstarch (Japanese Pharmacopeia) | 40 g |
| Crystalline cellulose (Japanese Pharmacopeia) | 20 g |
| Hydroxypropylcellulose (Japanese Pharmacopeia) | 4 g |
| Magnesium stearate (Japanese Pharmacopeia) | 2 g |

The above compound of the present invention, lactose, cornstarch and crystalline cellulose are mixed well and the mixture is granulated with 5% aqueous solution of hydroxypropylcellulose, and the granulated mixture is sieved with 200 mesh screen to dry the granules carefully, and then the granules are tabletted by a conventional method to give tablets (1000 tablets).

Pharmacological Experiments

The effects for suppression of the TNF-α-stimulated increased PTEN phosphorylation level by the representative compound of the present invention: cilostazol were tested Further, the effects on opening of Maxi-K channels of the representative compound of the present invention: cilostazol and some commercially available Maxi-K channels opener or blocker were tested.

Experiment 1

Effects of cilostazol on the suppression of the TNF-α-stimulated increase in PTEN phosphorylation level:

Materials:

Cell cultures: SK—N—SH (KCLB 30011, human brain neuroblastoma) cells were cultured in Eagle's minimum essential medium (MEM) with 2 mM L-glutamine and 1.0 mM sodium pyruvate supplemented with 10% heat-inactivated fetal bovine serum. Cells were grown to confluence at 37° C. in 5% $CO_2$ and used for experiments at no greater than passage 20.

Preparation of TNF-α solution: TNF-α (Upstate Biotechnology, Inc., Lake Placid, N.Y.) was dissolved in the phosphate buffered saline as a 10 μg/ml stock solution.

Method:

Western blot analysis: The confluent cells received MEM medium with 1% FBS plus cilostazol 3 hours prior to stimulation with TNF-α and then were exposed to TNF-α for one hour.

The cells were lysed in lysis buffer containing 50 mM Tris-Cl (pH 8.0), 150 mM NaCl, 0.02% sodium azide, 100 μg/ml phenylmethylsulfonyl fluoride, 1 μg/ml aprotinin and 1% Triton X-100. Following centrifugation at 12,000 rpm, 50 μg of total protein was loaded into 8 or 10% SDS-PAGE gel, and transferred to nitrocellulose membrane (Amersham Pharmacia Biotech, Piscataway, N.J.). The blocked membranes were then incubated with the indicated antibody, and the immunoreactive bands were visualized using chemiluminescent reagent as recommended by Supersignal West Dura Extended Duration Substrate Kit (Pierce, Rockford, Ill.). The signals of the bands were quantified using a GS-710 Calibrated imaging Densitomerter (Bio-Rad Laboratories, Hercules, Calif.). The results were expressed as a relative density. Polyclonal antibodies against PTEN, phospho-PTEN (Ser 380/Thr382/383) were from the Cell Signaling Technology (Beverly, Mass.).

Statistical analysis: The results are expressed as means±SEM. Statistical differences between groups were determined by Student's t-test. $p<0.05$ was considered to be significant.

Results:

The Western blot and densitometric analysis are shown in the accompanying FIG. 1.

As is seen from FIG. 1, cilostazol (1, 10 and 100 μM) concentration-dependently suppressed the TNF-α (50 ng/ml)-stimulated increased PTEN phosphorylation level.

From the above experimental results, it is clear that cilostazol showed potent activity of inhibiting PTEN phosphorylation.

Experiment 2

Materials:

Cell cultures: SK—N—SH (KCLB 30011, human brain neuroblastoma) cells were cultured in Eagle's minimum essential medium (HEM) with 2 mM L-glutamine and 1.0 mM sodium pyruvate supplemented with 10% heat-inactivated fetal bovine serum. Cells were grown to confluence at 37° C. in 5% $CO_2$ and used for experiments at no greater than passage 20.

Test drugs:

(1) Cilostazol (a compound of the present invention, a tradename of 6-[4-(1-cyclohexyl-1H-tetrazol-5-yl)-butoxy]-3,4-dihydro-carbostyril).

(2) Glibenclamide (abbreviated as "GBC", general name: Glyburide, chemical name: 5-chloro-N-[2-[4-[[[(cyclohexylamino)carbonyl]amino]sulfonyl]phenyl]ethyl]-2-methoxybenzamide, which is commercially available antidiabetics, a blocker of ATP-sensitive $K^+$ channels).

(3) Iberiotoxin (abbreviated as "Ibtx", which is known as Maxi-$K^+$ channel blocker).

Method:

Recording of the whole-cell $K^+$ current: The experiments were performed in a small bath (0.5 ml) mounted on the stage of an inverted microscope (Nikon model TE300, Tokyo, Japan) perfused continuously at a flow rate of 1 ml/min. Using the whole-cell configuration of the patch clamp technique, the K currents were recorded at room temperature (20~22° C.) with an Axopatch-200B patch clamp amplifier (Axon Instruments, Foster City, Calif.). Currents were sampled at 1 to 10 kHz after anti-alias filtering at 0.5 to 5 kHz. Data acquisition and command potentials were controlled by pClamp 6.0.3 software (Axon Instruments, Foster City, Calif.). To ensure the voltage clamp quality, electrode resistance was kept below 3 MΩ. Junction potentials were zeroed with the electrode in the standard bath solution. Gigaohm seal formation was achieved by suction and, after establishing the whole cell configuration, the capacitive transients elicited by symmetrical 10 mV voltage clamp steps from −80 mV were recorded at 50 kHz for calculation of cell capacitance. The normal bath solution for the whole-cell recordings was: NaCl 130 mM, KCl 5 mM, $MgCl_2$ 1.2 mM, $CaCl_2$ 1.8 mM, HEPES 10 mM, glucose 5.2 mM and the pH was adjusted to 7.4 with NaOH. Pipettes were filled with KCl 140 mM, $MgCl_2$ 0.5 mM, $CaCl_2$ 0.1 mM, ethylenebis(oxonitrilo) tetra-acetic acid (EGTA) 0.09 mM, HEPES 10 mM, glucose 10 mM and the pH was adjusted to 7.4 with KOH.

After establishment of whole-cell recordings and collecting control recordings for approximately 5 minutes until the current elicited by depolarization stabilized, cilostazol was applied to the bath. In the experiments, using glibenclamide or iberiotoxin, cilostazol was applied to the bath about 20 minutes after administering glibenclamide or iberiotoxin.

Figure 2:
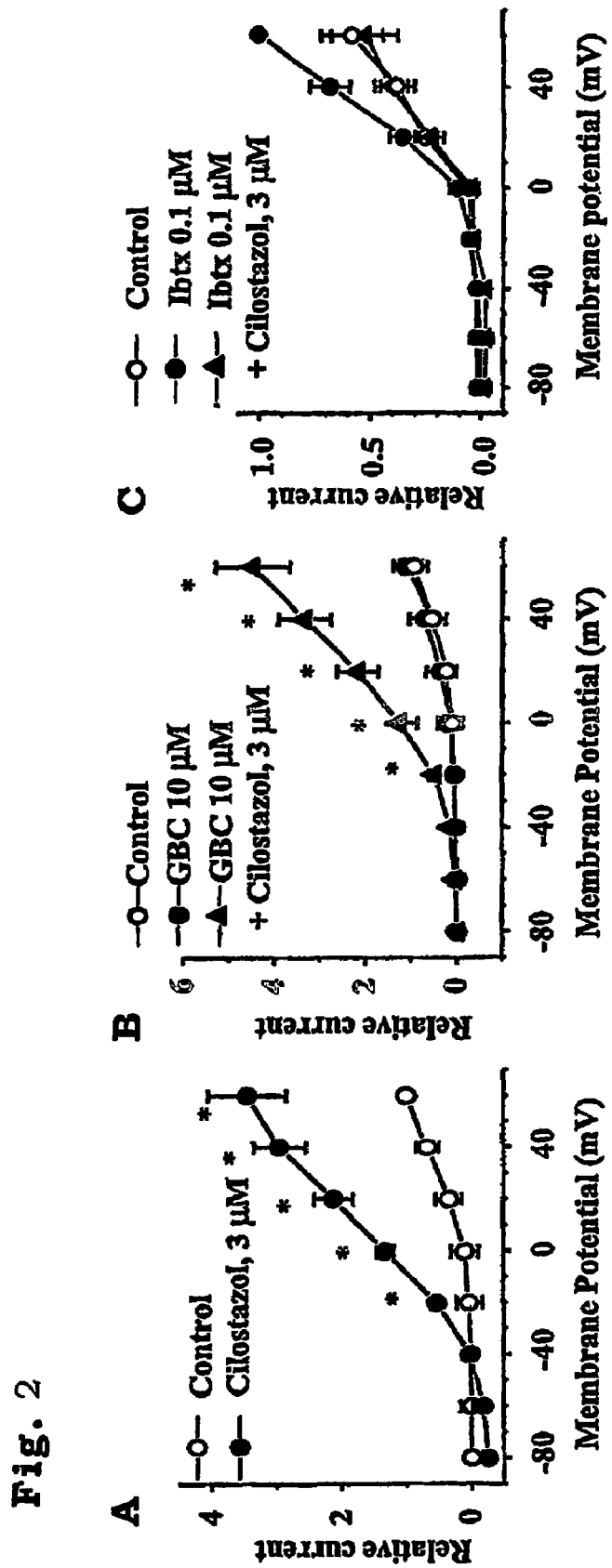
FIG. 2 shows effects of drugs on opening of calcium-activated K$^+$ current in SK—N—SH cells.

Results:

The test results are shown in the accompanying FIG. 2, wherein FIG. 2A shows the effects of cilostazol, FIG. 2B shows effects of cilostazol and/or glibenclamide ("GBC", suggestive of opening of Maxi-$K^+$ channels), and FIG. 2C shows effects of cilostazol and/or iberiotoxin ("Ibtx", Maxi-$K^+$ channel blocker).

As is seen from FIG. 2, the current was significantly increased by cilostazol, but on the other hand, it reversibly blocked by addition of iberiotoxin (100 nM) to the bath, but not by glibenclamide (10 μM). The increase in Maxi-K channel-medicated currents was given by cilostazol even in co-existence of glibenclamide, while glibenclamide alone could not increase the Maxi-K channel-mediated currents. When cilostazol was added to the cells together with iberiotoxin, Maxi-K channel blocker, increase of the current was rather less than iberiotoxin alone.

Experiment 3

1. Compound Preparation

Vehicle control; 0.5% carboxymethylcellurose. twice daily (n=10)

Cilostazol; 100 mg/kg,. twice daily (n=10)

Triturate a small amount of powder (cilostazol) by agate mortar. Add two or three drops of 0.5% carboxy-methylcel-lurose (CMC) and triturate well. Add 4-5 ml of 0.5% CMC and recover the suspended cilostazol to a light protected glass bottle.

Test compound preparation weekly at the concentration of 1000 mg/50 ml, and store protected from light at 4° C.

Compound Administration

Before administration, sonicate the stock bottle of test compound by ultra-sonic sonicator and mix well.

Compounds via twice daily oral gavage as per group assignments.

Vehicle Control (0.5% carboxymethylcellurose:CMC; 1 kg/5 ml) twice daily gavage. Test Compound (Cilostazol; 100 mg/kg/5 ml) twice daily gavage.

2. Methods of Observations, Examinations and Measurements a. The animals (8 weeks of age, Hemizygous transgenic mice that express mutant human $APP_{K670N,M6711}$/line Tg2576) were randomized into 2 groups of double transgenic APP/PS1 mice (control and cilostazol, total=20 mice). Each mouse was administered twice daily by gavage for 6 weeks, as shown in the following table:

| Protocol Design | | Number of | |
| --- | --- | --- | --- |
| Treatment | Start Age | Mice | Age at End |
| Control (Vehicle) | 8 weeks | 10 | 14 weeks |
| Test Compound | 8 weeks | 10 | 14 weeks |
| | Total Mice = 20 | | | b. Mice were genotyped at the beginning and end of the study.

c. Mice were subjected to the Y-maze behavior paradigm prior to completing the in-life phase.

d. The mice were sacrificed at 14 weeks of age.

e. Upon sacrifice, 1 ml of blood was collected for cilostazol blood concentration measurement, and APP/PS1 mice were perfused with saline. Brains were hemisected with one hemisphere fixed and the other hemisphere frozen.

f. The frozen hemisphere was homogenized and analyzed for total amyloid-beta concentration via ELISA.

Total A-Beta 40 and total A-Beta 42 levels in brains of mice were detected in the control group and, in cilostazol treated group. The results are shown in the accompanying FIG. 3.

3. Procedure

The following procedure outlines the steps taken to perform the test "Spontaneous Alternation in the Y-maze". Mice have an innate tendency to explore their environment. Successful exploration depends on the ability to avoid places recently visited, where food may have been depleted or absent ("spontaneous alternation"). The Y-maze is an ethologically based test that does not involve reward delivery. Mice with compromised "working memory" function cannot hold information regarding places just visited in their working memory; therefore they show decreased spontaneous alternation.

Published results have shown decreased spontaneous alternation and increased exploration in certain transgenic mouse strains, for example APP/PS1 mice.

Cilostazol has an anti-platelet and vaso-dilating action, which has an indication for ASO and prevention of secondary brain infarction.

These actions of Cilostazol may contribute to reduce the deposition of amyloid-beta protein, and improve a behavior of Alzheimer's dementia.

i. Bring mice to be tested into the testing room. Avoid bringing many mice (more than three cages) into the testing area at once, as this may influence their behavior. (Optional, do only if animals are not marked otherwise, e.g. by transponders or clearly visible tattoo.) Mark their tails with a non-toxic color marker in the following order:

1: red
2: green
3: blue
4: black ii. Experiments may be recorded by video. This produces a permanent record and allows the investigators to revisit the experiments if there are any questions.

iii. Take the first mouse to be tested out of its home cage by the base of the tail, and weigh it. Record the weight in the Y-Maze Data Spreadsheet. Place the mice back in the cage. (Alternatively, mice may be weighed before the start of the experiment, e.g. on the previous day)

iv. Leave the mice undisturbed for 1 hour before the testing starts so that they can acclimate to the room. Extra care should be taken to ensure that cages are not left adjacent to one particular arm, as the smell, for example, may influence the entry of a mouse into a single arm. Therefore, either place the cage at a distance from the apparatus or ensure that the cages are evenly distributed around the room. (eg. may introduce three cages at once ? one in proximity to each arm). Technician may be present in the testing room, but must not disturb the mice.

v. Before the test starts, wipe the inside of the Y-maze with isopropanol.

vi. Handle mice gently, holding by tail and let rest on arm, taking care not to let mouse plunge down head first into maze. Mice are individually placed in the center of a Y maze, with all three arms (arm A, arm B and arm C) available for exploration, for a period of 8 minutes.

vii. Record all entries on a printout of the Y-maze data sheet. Enter an "A" into the ARM ENTERED field if the mouse completely enters arm A, etc.

In the same row, enter "end" into OBSERVATIONS if the mouse explores the arm to the end, "R" for each time the mouse rears (sits on its hind legs with forelegs free) or "L" if it leans ("explores up the wall" with the forefeet touching the wall), and "F" if it freezes (remains motionless for 5 seconds or more). If the mouse goes back and forth within arm A, enter another "bf" in OBSERVATIONS in the same row. Enter any other observations in full text. If there is not enough time to enter observations, skip them. If the mouse returns to the center, start a new line. Enter "A" in the new line if mouse returns to arm A, "B" for arm B or "C" for arm C.

viii. After 8 minutes, remove the mice by the tail and place them in their home cage. Record the number of boli and whether or not the mice urinated in the Y-maze spreadsheet. Wipe the inside of the Y-maze with isopropanol. Use brush to get in corners, clean both walls and floor. Make sure that the Y-maze is clean and clear of any smell, bedding or food that may have been brought into the maze by a previous mouse. Make sure the Y-maze is dry after cleaning with alcohol. Make sure no cleaning material (such as tissue) is left behind in the maze.

ix. Repeat steps for all of the mice to be tested.

x. After the test, transfer data from hard copy to Excel spreadsheet.

The results obtained from the Y-maze behavior paradigm are summarized in the accompanying FIG. 4.

xi. Data analysis: An alternation is defined as a visit to all three arms without re-entry (ABC, ACB, BAC, BCA, CAB or CBA). Analyze each ARM ENTRY separately and determine whether it completed an alternation. The sequence ABCABC has four alternations, the first ends with C, the next with A, then B, then C. The sequence ABCBAC has only three alternations, the first ending in C, the second ending with A, and the third with C. % alternations is (number of observed alternations)/(number of possible alternations). If n arms are visited, the highest possible number of alternations is n-2. If the animal moves randomly, 22% alternations would be expected (3*2*1/3*3*3). Global activity is reflected in the total number of visits to the different arms. ACTIVITY is therefore (total number of arm entries)/minutes of observation).

Thus, the tetrazolylalkoxy-dihydrocarbostyril compounds (I) or a salt thereof of the present invention is effective for opening Maxi-K Channels and is useful for the treatment of neuronal disorders, particularly for the treatment of Alzheimer's disease.

INDUSTRIAL APPLICABILITY

The present invention provides a composition comprising as an active ingredient a tetrazolylalkoxy-dihydrocarbostyril compound (I) or a salt thereof, which has excellent PEN inhibitory effects and is useful as a medicament for promotion of the survival of normal cells, brain cells, heart cells, and skin, and further for inhibiting of Gram negative sepsis and cell migration and cell invasion without any side effect due to inhibition of PTEN. The composition of the present invention is further useful as an opener of a large conductance $Ca^{2+}$-activated $K^+$ channel (Maxi-K channel) and hence as a medicament for the treatment of neuronal disorders, for example, an anti-convulsant, a neuroprotecting agent, a medicament for treatment of regional cerebral edema and neurologic motor impairment, cognitive disorders, traumatic brain injury, Parkinson's disease, epilepsy, migraine, and Alzheimer's disease, etc.

The invention claim is:

1. A method for treating a patient with an Alzheimer's disease comprising administering to said patient an effective amount of a tetrazolylalkoxy-dihydrocarbostyril compound (I)

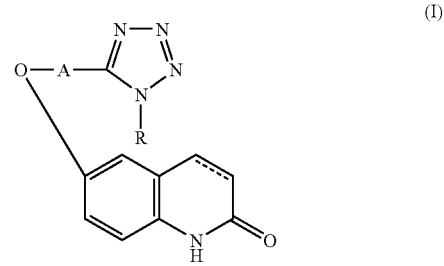

wherein R is a cycloalkyl group, A is a lower alkylene group, and the bond between 3- and 4-positions of the carbostyril nucleus means a single bond or a double bond, or a salt thereof.

2. The method according to claim 1, wherein the compound is 6-[4-(1-cyclohexyl-1H-tetrazol-5-yl)butoxy]-3,4-dihydrocarbostyril or a salt thereof.

* * * * *